United States Patent
Thieme-Marti et al.

(10) Patent No.: US 11,590,366 B2
(45) Date of Patent: Feb. 28, 2023

(54) LIVE VIEW CAMERA FOR RADIATION THERAPY

(71) Applicant: Varian Medical Systems, Inc., Palo Alto, CA (US)

(72) Inventors: Stefan J. Thieme-Marti, Baden (CH); Mathias Lehmann, Zurich (CH)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 17/336,037

(22) Filed: Jun. 1, 2021

(65) Prior Publication Data
US 2021/0379407 A1    Dec. 9, 2021

Related U.S. Application Data

(60) Provisional application No. 63/036,962, filed on Jun. 9, 2020.

(51) Int. Cl.
*A61N 5/10* (2006.01)

(52) U.S. Cl.
CPC .... *A61N 5/1049* (2013.01); *A61N 2005/1059* (2013.01); *A61N 2005/1094* (2013.01)

(58) Field of Classification Search
None
See application file for complete search history.

(56) References Cited

U.S. PATENT DOCUMENTS

| 4,675,731 | A | * | 6/1987 | Takasu | H04N 5/3205 378/98.12 |
| 7,502,443 | B1 | * | 3/2009 | Haynes | A61N 5/1049 378/68 |
| 2008/0267471 | A1 | * | 10/2008 | Yu | G06T 7/0012 382/128 |
| 2009/0135386 | A1 | * | 5/2009 | Nishikawa | G03F 7/70908 355/30 |
| 2021/0015441 | A1 | * | 1/2021 | Bourne | A61B 6/4208 |

* cited by examiner

*Primary Examiner* — Hoon K Song
(74) *Attorney, Agent, or Firm* — Harness, Dickey & Pierce P.L.C.

(57) ABSTRACT

An apparatus for use with a medical system, the medical system comprising a medical device configured to treat and/or image a patient, includes: a camera configured to capture an image of a first mirror, wherein the image of the first mirror contains an image of at least a part of the patient and/or an image of at least a part of the medical system; wherein the camera comprises electronics that are not radiation-hard.

17 Claims, 11 Drawing Sheets

LIVE VIEW CAMERA FOR RADIATION THERAPY

RELATED APPLICATION DATA

This application claims priority to, and the benefit of, U.S. Provisional Patent Application No. 63/036,962, filed on Jun. 9, 2020. The entire disclosure of the above application is expressly incorporated by reference herein.

FIELD

The field relates to optical devices for use in medical processes, and more particularly, to cameras and methods for use in medical treatment, such as radiation therapy.

BACKGROUND

Radiation therapy involves medical procedures that selectively expose certain areas of a human body, such as cancerous tumors, to doses of radiation. The purpose of the radiation therapy is to irradiate the targeted biological tissue such that undesirable tissue is destroyed. Radiation has also been-used to obtain images of tissue for diagnostic or treatment purposes.

During delivery of radiation towards a patient, it may be desirable to ensure that a patient remains at a certain position. Also, it may be desirable to know the position of a patient and/or the position of various components of the treatment system during the treatment session in order to prevent collision between the patient and the components.

SUMMARY

Cameras may be used in treatment room or an imaging room to monitor position of a patient and/or components of medical system. However, these cameras may be damaged over time due to exposure to ionizing radiation resulted from operation of the medical system. Cameras may be made to include radiation-hard electronics in order to make the cameras resistant to damage or malfunction caused by ionizing radiation. However, the process of radiation hardening to make electronic components resistant, or to at least increase their ability to resist ionizing radiation, is expensive.

In one or more embodiments described herein, an apparatus comprising a camera may be provided to monitor a patient, and/or components of a medical system. The medical system may comprise a medical device, such as a radiation treatment machine, configured to treat the patient, or may comprise an imaging machine configured to image the patient. In some embodiments, the camera may not include radiation-hard electronics. In one implementation, the camera may be an off-the-shelf camera. To prevent radiation resulted from an operation of the medical device from damaging the sensor of the camera, or to at least reduce a degree of damage done by the radiation to the sensor of the camera, the camera may be configured to view one or more mirrors. The one or more mirrors reflect an image of at least a part of the patient and/or an image of at least a part of the medical system, which image(s) is captured by the camera. The apparatus may also include shielding covering a part of the camera while allowing the camera to view a treatment environment via the one or more mirrors. The mirror(s) and the shielding may obviate the need for providing radiation-hard electronics for the camera, or may at least reduce the level of requirement for radiation-hard electronics.

An apparatus for use with a medical system, the medical system comprising a medical device configured to treat and/or image a patient, includes: a camera configured to capture an image of a first mirror; wherein the image of the first mirror contains an image of at least a part of the patient and/or an image of at least a part of the medical system.

Optionally, the camera comprises electronics that are not radiation-hard or that are partially radiation-hard.

Optionally, the apparatus further includes a shielding covering a part of the camera, wherein the shielding is configured to block at least some radiation resulted from an operation of the medical device.

Optionally, the shielding and the first mirror are configured to obviate a need to provide radiation-hard electronics for the camera.

Optionally, the shielding comprises an opening aligned with a viewing path of the camera, wherein the opening is configured to allow the camera to view the first mirror.

Optionally, the apparatus further includes a processing unit configured to receive an image frame comprising the image of the first mirror from the camera.

Optionally, the processing unit is also configured to remove a part of the image frame that does not contain the image of the first mirror.

Optionally, the processing unit is also configured to split the image of the first mirror into sub-images.

Optionally, the processing unit is configured to process the image frame from the camera to monitor a position of the patient, to monitor a physiological state of the patient, to monitor a position of a component of the medical system, to prevent a collision between the medical device and the patient, to prevent a collision between the medical device and a patient support, or any combination of the foregoing.

Optionally, the apparatus further includes the first mirror.

Optionally, the first mirror comprises a flat mirror.

Optionally, the first mirror comprises a curvilinear mirror.

Optionally, the first mirror comprises an asymmetric mirror.

Optionally, the first mirror is detachably coupled to a part of the apparatus.

Optionally, the camera is also configured to capture an image of a second mirror.

Optionally, the camera is configured to capture the image of the first mirror and the image of the second mirror simultaneously.

Optionally, the apparatus further includes the first mirror and the second mirror, wherein the first mirror and the second mirror have different respective curvatures.

Optionally, the apparatus further includes the first mirror and the second mirror; wherein the first mirror has a planar configuration that is either rectilinear or curvilinear, and the second mirror has a partial spherical shape, a partial aspherical shape, a partial or a complete symmetrical cone shape, or a partial or a complete asymmetrical cone shape.

Optionally, the apparatus further includes a processing unit configured to process an image frame from the camera, wherein the image frame comprises the image of the first mirror and the image of the second mirror.

Optionally, the image of the first mirror contains a first scenery image reflected off from the first mirror, and the image of the second mirror contains a second scenery image reflected off from the second mirror; and wherein the processing unit is configured to process the first scenery image and the second scenery image using different respective processing algorithms.

Optionally, the apparatus is configured to be mounted to a patient support.

Optionally, the camera is configured to be mounted to the medical device, and herein the medical device is a treatment machine or an imaging machine.

Optionally, the camera is configured to be mounted directly or indirectly to a wall, a ceiling, a beam, or a column.

Optionally, the electronics that are not radiation-hard comprise optical sensors of the camera.

An apparatus for use with a medical system, the medical system comprising a medical device configured to treat and/or image a patient, includes: a camera configured to capture an image of a first mirror, wherein the image of the first mirror contains an image of at least a part of the patient and/or an image of at least a part of the medical system; and a processing unit configured to receive an image frame from the camera, the image frame comprising the image of the first mirror; wherein the processing unit is also configured to extract the image of the first mirror from the image frame, and process the image of the first mirror to monitor a position of the patient, to monitor a physiological state of the patient, to monitor a position of a component of the medical system, to prevent a collision between the medical device and the patient, to prevent a collision between the medical device and a patient support, or any combination of the foregoing.

A method performed by an apparatus that is configured for use with a medical system, the medical system comprising a medical device configured to treat and/or image a patient, includes: capturing an image of a first mirror, wherein the image of the first mirror contains an image of at least a part of the patient and/or an image of at least a part of the medical system; and processing the image of the first mirror to monitor a position of the patient, to monitor a physiological state of the patient, to monitor a position of a component of the medical system, to prevent a collision between the medical device and the patient, to prevent a collision between the medical device and a patient support, or any combination of the foregoing.

Other and further aspects and features will be evident from reading the following detailed description.

BRIEF DESCRIPTION OF THE DRAWINGS

The drawings illustrate the design and utility of embodiments, in which similar elements are referred to by common reference numerals. In order to better appreciate how advantages and objects are obtained, a more particular description of the embodiments will be described with reference to the accompanying drawings. Understanding that these drawings depict only exemplary embodiments and are not therefore to be considered limiting in the scope of the claimed invention.

DESCRIPTION OF THE EMBODIMENTS

Figure 1:
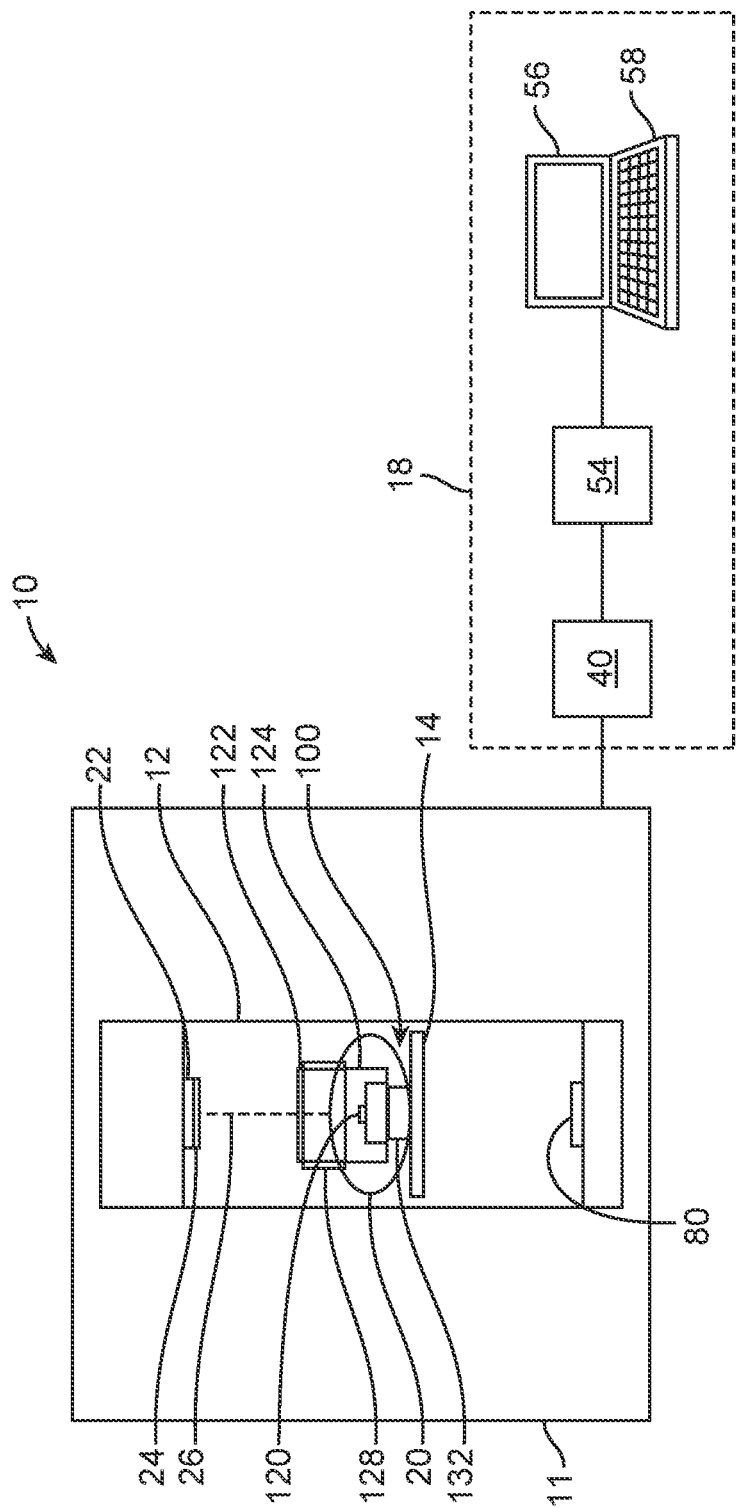
FIG. 1 illustrates a medical system and an apparatus comprising a camera for use with the medical system.

Various embodiments are described hereinafter with reference to the figures. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages of the invention shown. An aspect or an advantage described in conjunction with a particular embodiment is not necessarily limited to that embodiment and can be practiced in any other embodiments even if not so illustrated or if not so explicitly described.

FIG. 1 illustrates a medical system 10. In the illustrated embodiments, the medical system 10 is a radiation treatment system, and it includes a medical device 11 and a patient support 14 for supporting a patient 20. The medical device 11 includes an arm gantry 12 and a control system 18 for controlling an operation of the gantry 12 and delivery of radiation. The medical device 11 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate proton beam as a form of radiation for treatment purpose. Also, in other embodiments, the system 10 may have other form and/or configuration. For example, in other embodiments, instead of an arm gantry 12, the medical device 11 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may also be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to provide X-ray radiation at a plurality of photon energy levels within a range anywhere between approximately 10 keV and approximately 20 MeV. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. In some cases, the control 40 may also control the collimator system 22 and the position of the patient support 14. In addition, in some cases, the control 40 may be configured to control the beam 26 (e.g., beam hold for gating). Furthermore, the control 40 may be configured to control an imaging process (e.g., triggering of imaging). Although the control 40 is shown as a separate component from the gantry 12 and the processing unit 54, in alternative embodiments, the control 40 can be a part of the gantry 12 or the processing unit 54.

In some embodiments, the medical system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

In other embodiments, the medical system 10 may be an imaging system configured to deliver imaging radiation beam towards the patient 20 for imaging the patient 20.

Figure 2:
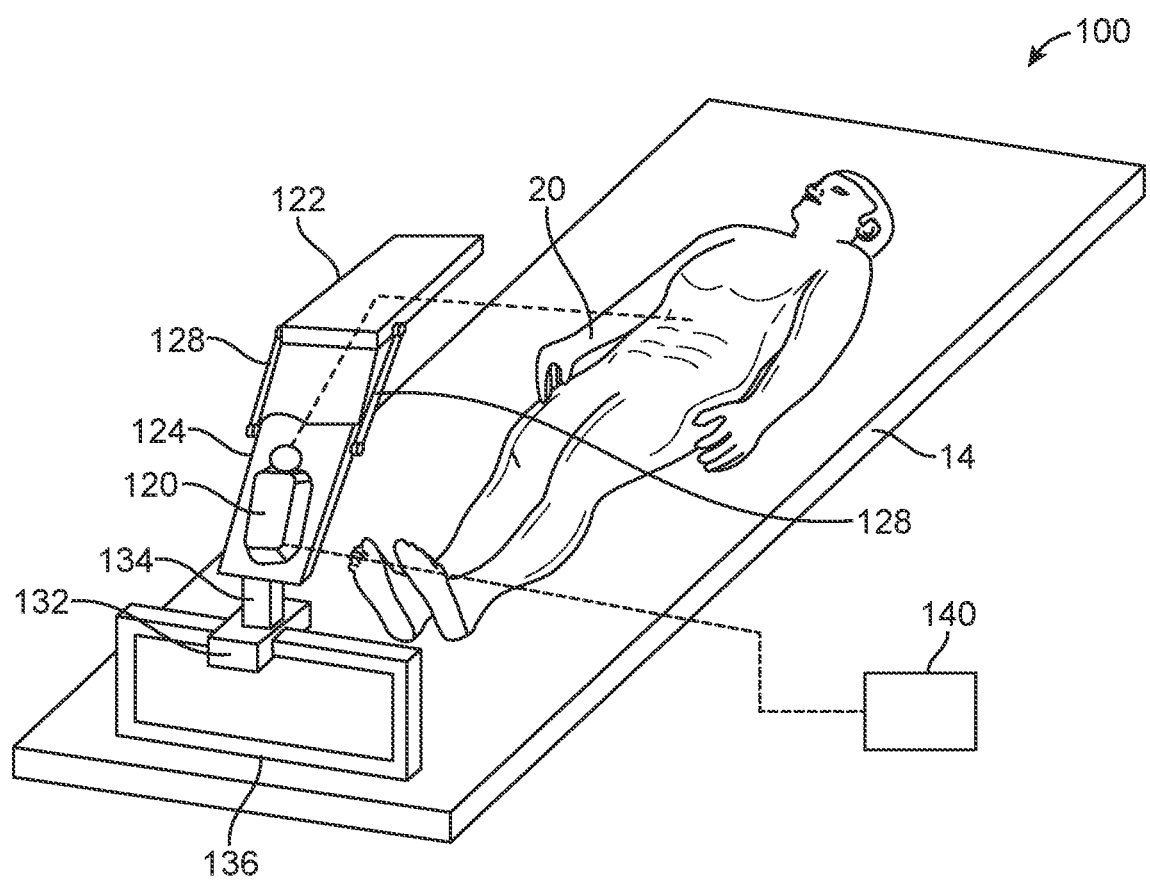
FIG. 2 illustrates the apparatus of claim 1, particularly showing the camera of the apparatus being mounted to a patient support.

As shown in FIGS. 1 and 2, an apparatus 100 is provided for use with the medical system 10. The apparatus 100 includes a camera 120 configured for viewing a mirror 122. The apparatus 100 also includes a securing mechanism 132 for securing the camera 130 relative to an object, and a support 134. The camera 120 is configured to view its surrounding environment via the mirror 122. For example, the camera 120 may be configured to view the patient 20 and/or any component(s) of the medical system 10 by capturing images in the mirror 122. The mirror 122 is oriented so that image of the patient 20 and/or image of any component(s) of the medical system 10 is reflected off the mirror 122 for capture by the camera 120.

As shown in the figure, the apparatus 100 also includes a shielding 124 covering at least a part of the camera 120. The apparatus 100 is configured for use with a medical system that comprises a medical device configured to treat and/or image a patient. The shielding 124 is configured to block at least some radiation resulted from an operation of a medical device. During use, the camera 120 is configured to capture an image of the mirror 122, wherein the image of the mirror 122 contains an image of at least a part of the patient and/or an image of at least a part of the medical system. In particular, because the mirror 122 is configured to reflect image of object(s) of interest for viewing by the camera 120, the image of the mirror 122 as captured by the camera 120 contains image of object(s) of interest.

In the illustrated embodiments, the shielding 124 and the mirror 122 are configured to obviate a need to provide radiation-hard electronics for the camera 120. Thus, in some embodiments, the camera 120 comprises electronics that are not radiation-hard. As used in this specification, the term "radiation-hard" refers to a characteristic of electronics that have been processed (e.g., treated) or made to withstand radiation (e.g., ionizing radiation) for a designed duration. The designed duration for the camera to withstand radiation may be at least: 1 year, 2 year, 3 year, 4 year, 5 year, 6 year 7 year, 8 year, 9 year, 10 year, 11 year 12 year, 13 year, 14 year, 15 year, 16 year, 17 year, 18 year, 19 year, 20 year, etc. In some case, the designed duration may be at least 50% (e.g., 100%) of a duration of a designed useful life of the camera 120. Electronics that are not radiation-hard refer to electronics that has not been treated or made to withstand radiation. In some embodiments, the electronics that are not radiation-hard may be optical sensors of the camera 120. In other embodiments, the camera 120 may include electronics that are partially or fully radiation-hard. Electronics that are partially radiation-hard refer to electronics that have been processed or made to withstand some radiation, or to withstand radiation for a duration that is less than a designed duration of a fully radiation-hard electronics. View differently, electronics that are partially radiation-hard refer to electronics that have better radiation-resistance ability than electronics that are not radiation-hard. In some cases, because the mirror 122 allows the camera 120 to image object(s) of interest while preventing radiation from directly reaching the camera 120, the level of radiation-hard for the electronics may be reduced (compared to the scenario in which no mirror is used).

In some embodiments, the shielding 124 may comprise an opening aligned with a viewing path of the camera 120, wherein the opening is configured to allow the camera 120 to view the mirror 122.

As shown in FIG. 2, the apparatus 100 further includes a processing unit communicatively coupled to the camera 120. The processing unit 140 may be configured to receive an image frame comprising the image of the mirror 122 from the camera 120. In some embodiments, the processing unit is also configured to remove a part of the image frame that does not contain the image of the mirror 122.

In some embodiments, the processing unit 140 is configured to process the image frame from the camera 120 to monitor a position of the patient 20, to monitor a physiological state of the patient 20, to monitor a position of a component of the medical system 10, to prevent a collision between the medical device and the patient 20, to prevent a collision between the medical device and a patient support 14, or any combination of the foregoing.

In some embodiments, the mirror 122 may form part of the apparatus 100. In such cases, the apparatus 100 further includes the mirror 122. In other embodiments, the apparatus 100 does not include the mirror 122. In some embodiments, the mirror 122 is detachably coupled to the camera 120. Also, in some embodiments, the mirror 122 is moveably coupled to the camera 120. This allows a relative position and/or a relative orientation between the mirror 122 and the camera 120 to be selectively adjustable. In one implementation, such as that shown in FIG. 2, the mirror 122 is rotatably coupled to the shielding 124 via arms 128. This allows an orientation of the mirror 122 relative to the camera 120 to be adjusted. Also, in some embodiments, a relative distance between the mirror 122 and the camera 120 may be selectively adjustable. For example, the mirror 122 and the camera 120 may be coupled to each other via a telescopic mechanism, a moveable arm system, a cable system, etc., which allows a distance between the mirror 122 and the camera 120 to be adjusted.

In the illustrated embodiments, the mirror 122 comprises a flat mirror. The flat mirror may have a rectilinear configuration (i.e., completely flat), or may have a slight curvature. In other embodiments, the mirror 122 comprises a curvilinear mirror (e.g., a mirror with a curvilinear surface). The mirror 122 may be a symmetric mirror or an asymmetric mirror. The mirror 122 may have a variety of different shapes in different embodiments. By means of non-limiting examples, the mirror 122 may have a partial spherical shape, a partial aspherical shape, a partial or a complete symmetrical cone shape, or a partial or a complete asymmetrical cone shape, etc. The mirror 122 may be an off-the-shelf mirror in some embodiments. In other embodiments, the mirror 122 may be a custom-made mirror having specific size, shape, and mirror surface curvature. In some embodiments, the mirror 122 may be manufactured using 3D printing technique and polymer smoothing technique.

In some embodiments, the dimensions of the camera 120 may be small enough to be non-intrusive to the treatment process when mounted during use. For example, in some embodiments, the camera 120 may have a dimension of 11 inch×2.5 inch×1.5 inch. In other embodiments, the camera 120 may have other dimensions, such as those larger or smaller than the example provided above, as long as the use of the camera 120 does not interfere with the treatment and/or imaging procedure.

Also, in some embodiments, the camera 120 may be infrared-based, in which cases, the camera 120 may view the patient and/or any component(s) of the system 10 even in dim or dark environment. In some embodiments, the camera 120 may be configured to output infrared video images for viewing by a user.

In some embodiments, the camera 120 may include one or more light sources. For example, the camera 120 may include visible light source(s), and/or non-visible light source(s). A non-visible light source may be configured to emit infrared light or UV light. Also, a light source of the camera 120 may be configured to provide structured light or non-structured light. The non-structured light may be projected onto the patient, onto a marker device coupled to the patient, onto a component of the medical system 10, onto a marker device coupled to the medical system 10, onto an accessory of the medical system 10, or any combination of the foregoing.

Furthermore, in some embodiments, the camera 120 may include an infrared emitter, a color sensor, and an infrared sensor. The infrared sensor is configured to sense image based on infrared light output by the infrared emitter. The color sensor is configured to sense visible image.

The support 134 and the securing mechanism 132 allow the camera 120 to be detachably coupled to the patient support 14. The support 134 may be a post, a bracket, a beam, an arm, etc., for supporting the camera 120. The securing mechanism 132 may be located at the support 134. Also, in some embodiments, the support 134 may optionally have one or more moveable parts to allow a position and/or an orientation of the camera 120 to be adjusted relative to the support 14 (or relative to the patient 20 or another reference location). In some embodiments, the support 134 itself may be movable relative to the patient support 14 in order to adjust the camera position (e.g., longitudinally) relative to the patient 20. In further embodiments, the support 134 may be a base with a tilt motor, which allows the camera 120 to be tilted in one, two, or three, degrees of movement relative to the base. In other embodiments, the support 134 is not needed, and the medical system 100 may not include the support 134.

In other embodiments, the camera 120 may be permanently coupled to the patient support 14, or to a component (e.g., gantry, energy source, imaging panel, etc.) of the medical system 100. The camera 120 may be fixedly or moveably coupled to the patient support 14 or to the component of the medical system 100. If the camera 120 is moveably coupled to the patient support 14 or to the component of the medical system 100, the relative orientation of the camera 120 relative to the patient support 14 or relative to the component of the medical system 100 may be selectively adjustable so that the camera 120 may be rotated about a first axis (e.g., X-axis), a second axis (e.g., Y-axis), a third axis (e.g., Z-axis), or any combination of the foregoing. Additionally, or alternatively, the relative orientation of the camera 120 relative to the patient support 14 or relative to the component of the medical system 100 may be selectively adjustable so that the camera 120 may be translated along a first axis (e.g., X-axis), a second axis (e.g., Y-axis), a third axis (e.g., Z-axis), or any combination of the foregoing.

In the above embodiments, the camera 120 is illustrated as being configured to be mounted to the patient support 14. In other embodiments, the camera 120 may be configured to be mounted to the medical device, such as a treatment machine or an imaging machine. In further embodiments, the camera 120 may be configured to be mounted directly or indirectly to a wall, a ceiling, a beam, or a column.

Figure 3:
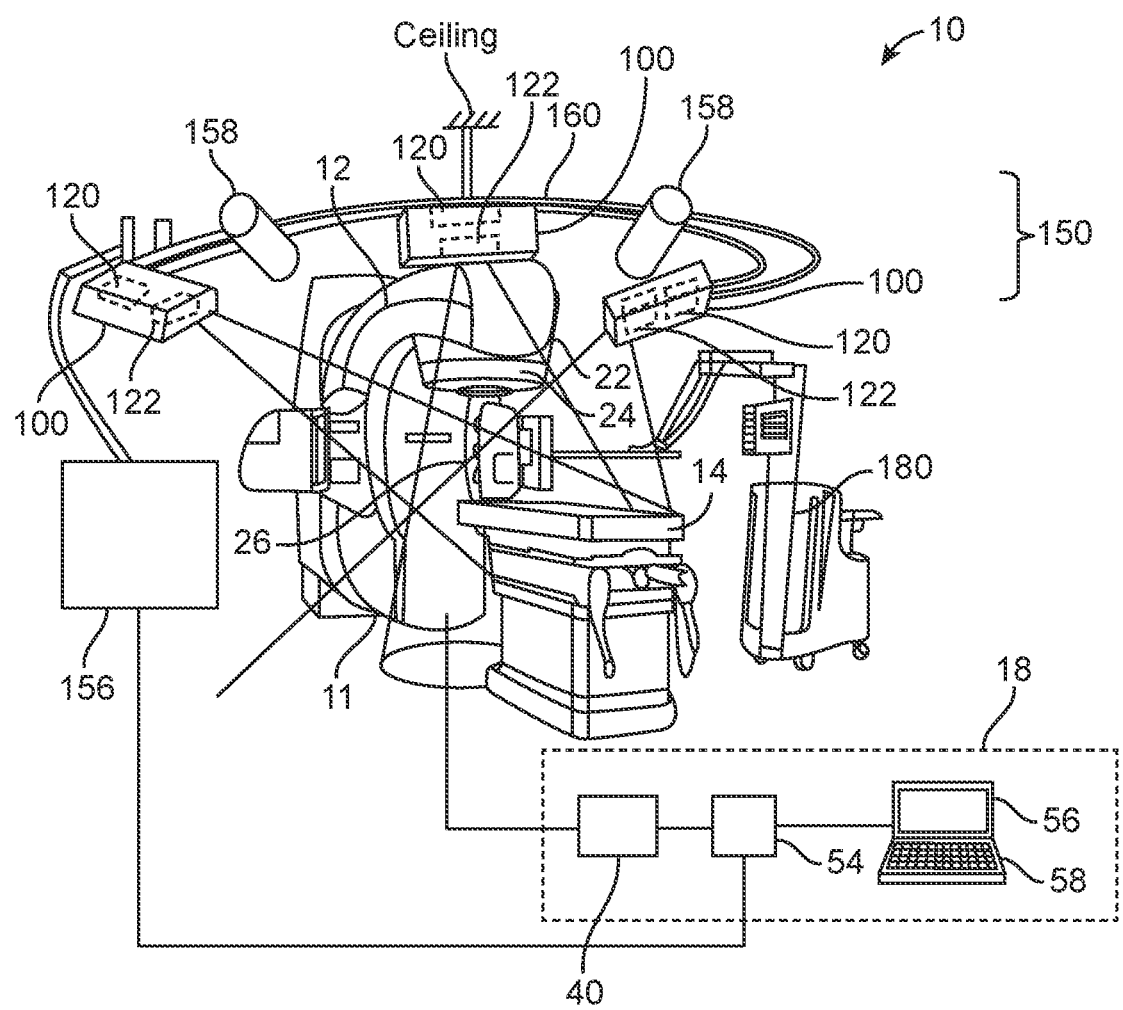
FIG. 3 illustrates another medical system and an apparatus comprising a camera for use with the medical system.

In some embodiments, an optical system may be provided that includes multiple apparatuses 100. Each apparatus 100 includes a camera 120 and a mirror 122. FIG. 3 illustrates a medical system 10 that includes an optical system 150. The medical system 10 is a treatment system that includes a medical device 11 and a patient support 14 for supporting a patient (not shown). The medical device 11 includes a gantry 12, and a control system 18 for controlling an operation of the gantry 12. The medical system 10 of FIG. 3 may be an example of the medical system 10 of FIG. 1.

As shown in FIG. 3, the optical system 150 includes multiple apparatuses 100, wherein each apparatus 100 includes a camera 120 and a mirror 122. The optical system 140 also includes a processing unit 156 in communication with the cameras 120. The processing unit 156 may be an example of the processing unit 140 of FIG. 2 in some embodiments. In the illustrated example of FIG. 3, the optical system 150 has three apparatuses 100 with respective cameras 120 and mirrors 122. In other embodiments, the optical system 150 may have fewer than three apparatuses 100 (e.g., one apparatus 100 or two apparatuses 100), or more than three apparatuses 100.

Also, in some embodiments, the optical system 150 may include one light source or multiple light sources (not shown) for respective cameras 120. In some embodiments, there may be multiple light sources integrated with respective cameras 120. For example, in one implementation, the optical system 150 may include multiple pods, wherein each pod may have one or more light sources and one or more cameras 120 (e.g., two cameras 154).

Also, in some embodiments, the light provided by the light source may be in an infrared range (e.g., having infrared wavelength(s)). This technique obviates the need to use very intense light source(s), which may "blind" the patient, particularly during head, neck, and breast treatments in which the light is directed towards the upper part of the patient. In other embodiments, the light source may be configured to provide non-visible light having other wavelengths (e.g., ultraviolet light). Also, use of non-visible light is advantageous because unlike video-based system that uses visible wavelengths, it does not exhibit stroboscopic effects that may confuse the patient, and it does not trigger symptoms of motion sickness.

Figure 4:
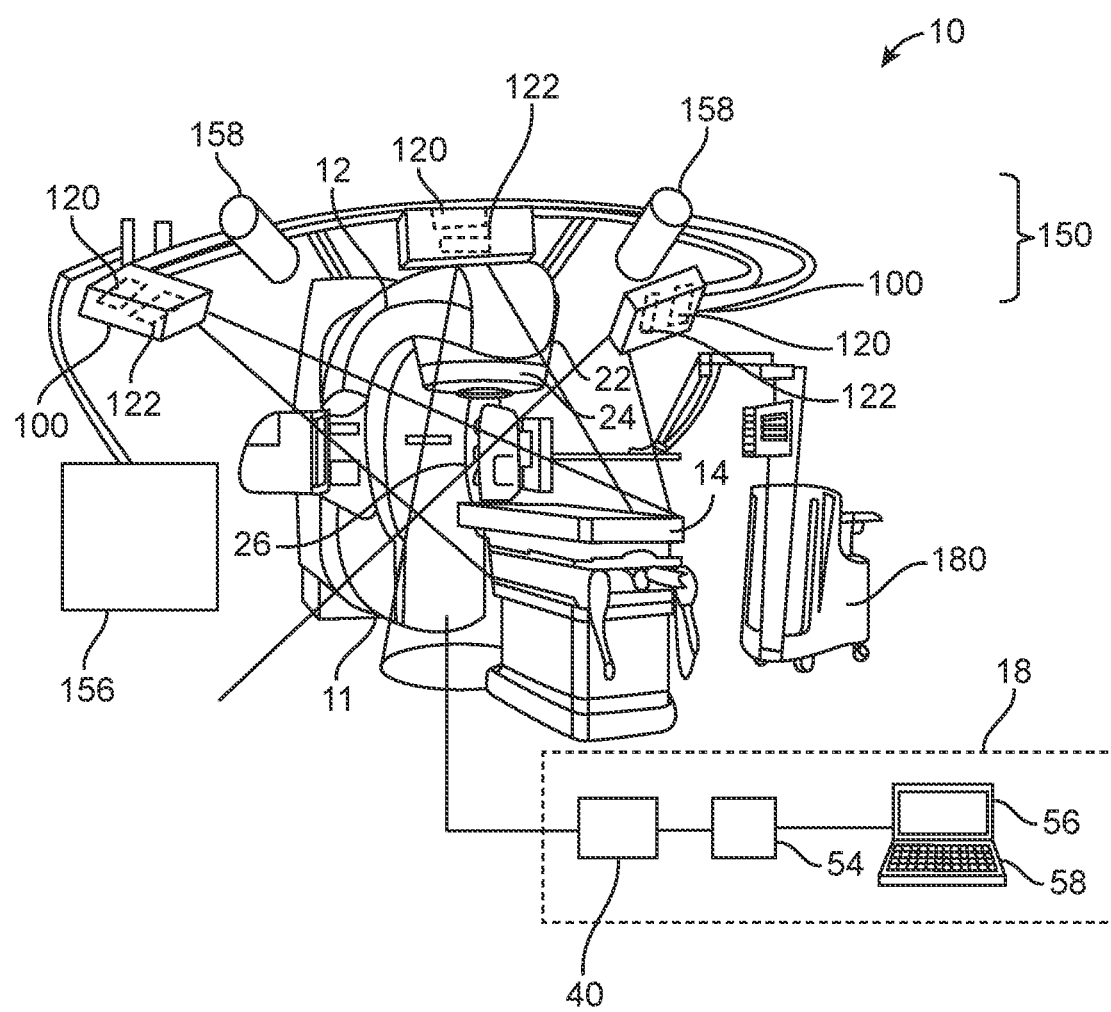
FIG. 4 illustrates another medical system and an apparatus comprising a camera for use with the medical system.

The optical system 150 may also optionally include a frame 160 to which the apparatuses 100 may be mounted. The frame 160 may be mounted to a ceiling and/or a wall of a room in which the treatment system 10 is located. Alternatively, the frame 160 may be mounted to the treatment system 10 (FIG. 4). The apparatuses 100 (e.g., the cameras 120) and the frame 160 may be preassembled at a factory, which allows easy installation at the medical facility. The cameras 120 may be moveably mounted to the frame 160. In one implementation, each of the cameras 120 may be rotatably mounted to the frame 160 (e.g., via a ball joint) so that the camera 120 is rotatable about one or more axes with respect to the frame 160. Similarly, one or more light sources may be moveably mounted to the frame 160. For example, a light source may be rotatably mounted to the frame 160 (e.g., via a ball joint) so that the light source is rotatable about one or more axes with respect to the frame 160. In other embodiments, instead of ball joints, the cameras 120 and the light source(s) may be moveably mounted to the frame 160 using other connectors, such as arms, so that the cameras 120 and the light source(s) are moveable with respect to the frame 160. In other embodiments, the one or more of the cameras 120 and/or the light source(s) may be mounted directly to the treatment system 10 or a room.

As shown in FIGS. 3-4, the optical system 150 may also include a plurality of time-of-flight (TOF) cameras 158. Each TOF camera 158 is configured to provide depth image(s). A depth image has pixel values representing a distance between a reference point and a surface point detected. In some embodiments, each TOF camera 158 may be an infrared camera. During use, images from the cameras 120 and the TOF cameras 158 are processed by the processing unit 156 to obtain and monitor surface contours of the patient before and during treatment for the purpose of patient setup (absolute positioning and/or relative positioning), patient monitoring during treatment (e.g., monitoring absolute position and/or relative position), tool surveillance, prevention of patient-machine collisions, or a combination of the foregoing. Patient monitoring may include: (1) ensuring that the patient does not leave its setup position, and/or (2) recording a periodic patient motion due to breathing, and controlling a machine accordingly (e.g., beam hold, multi-leaf collimator tracking, tracking of patient support, etc.).

In some cases, the TOF cameras 158 may help increase a field of view, and may observe blind spots not captured by the camera(s) 120.

In some embodiments, the TOF cameras 158 may provide images at lower resolution than that of the images provided by the cameras 120. In other embodiments, the TOF cameras 158 may provide images at higher resolution than that of the images provided by the cameras 120.

In the illustrated example, the optical system 150 has two TOF cameras 158. In other embodiments, the optical system 150 may include more than two (e.g., three, four, etc.) TOF cameras 158, or fewer than two (i.e., one) TOF camera 158.

The TOF cameras 158 may be moveably mounted to the frame 160. In one implementation, each of the TOF cameras 158 may be rotatably mounted to the frame 160 (e.g., via a ball joint) so that the TOF camera 158 is rotatable about one or more axes with respect to the frame 160. In other embodiments, instead of ball joints, the TOF cameras 158 may be moveably mounted to the frame 160 using other connectors, such as arms, so that the TOF cameras 158 are moveable with respect to the frame 160. In other embodiments, the one or more of the TOF cameras 158 may be mounted directly to the treatment system 10 or a room.

In other embodiments, the TOF cameras 158 may be mounted to different frame than that of the optical system 150. Also, in further embodiments, the TOF cameras 158 may be configured to be mounted to the medical system 10, e.g., to the gantry, to the patient support. In some cases, the TOF cameras 158 may be mounted to deployable arms that are coupled to the medical system 10. In other embodiments, the TOF cameras 158 may be mounted to a room (e.g., to a wall, a ceiling, a floor, etc.).

In other embodiments, the optical system 150 may not include any TOF cameras 158.

In some embodiments, the optical system 150 may include multiple pods, wherein each pod may have one or more cameras 120 (e.g., two cameras 154), and one or more mirrors 122. In some embodiments, each pod may optionally also include one or more TOF cameras 158, and/or one or more light sources. In some embodiments, the pod(s) may be mounted to a frame of the optical system 150. In other embodiments, the pod(s) may be mounted to a different frame than that of the optical system 150. Also, in further embodiments, the pod(s) may be configured to be mounted to the medical system 10, e.g., to the gantry, to the patient support. In some cases, the pod(s) may be mounted to deployable arms that are coupled to the medical system 10. In other embodiments, the pod(s) may be mounted to a room (e.g., to a wall, a ceiling, a floor, etc.).

The optical system 150 may be configured to provide patient setup, patient monitoring, device monitoring, respiratory motion control, patient-machine collision prevention, or any combination of the foregoing. Thus, in some cases, the same optical system 150 may provide multiple purposes. In some embodiments, different clinical use cases mentioned above may be performed simultaneously. In one implementation, the sequence of real-time input images from the camera(s) 120 and from the TOF camera(s) 158 may be processed by the processing unit 156 to perform patient-machine collision prevention. The same real-time input images (or a subset of them) from the camera(s) 120, and the same real-time input images (or a subset of them) from the TOF camera(s) 158 may also be processed by the processing unit 156 to perform patient monitoring and/or device monitoring. Also, in some embodiments, by combining external surface information of the patient (provided by the optical system 150) with x-ray imaging of the internal anatomy, highly integrated and automated treatment workflows may be achieved.

In other embodiments, the optical system 150 does not include the TOF cameras 158, and the optical system 150 is configured to process images from the camera(s) 120 to provide patient setup, patient monitoring, device monitoring, respiratory motion control, patient-machine collision prevention, or any combination of the foregoing.

Figure 5:
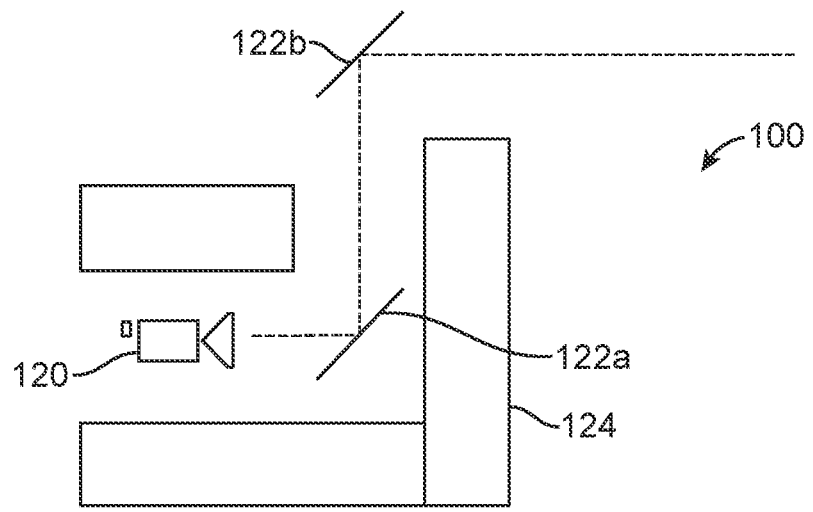
FIG. 5 illustrates an example of an apparatus that includes a camera viewing a mirror.

In the above embodiments, the mirror 122 is configured to reflect image of object(s) of interest for viewing by the camera 120. In other embodiments, the apparatus 100 may include multiple mirrors 122. In such cases, the mirrors 122 cooperate with each other to reflect image of object(s) of interest for viewing by the camera 120. FIG. 5 illustrates an example of an apparatus 100 that includes a camera 120 viewing a first mirror 122a. The apparatus 100 also includes a second mirror 122b for reflecting images to the first mirror 122a. As shown in the figure, the apparatus 100 also includes a shielding 124 covering at least a part of the camera 120. The apparatus 100 is configured for use with a medical system that comprises a medical device configured to treat a patient. The shielding 124 is configured to block at least some radiation resulted from an operation of a medical device. During use, the camera 120 is configured to capture an image of the first mirror 122a, wherein the image of the first mirror 122a contains an image of at least a part of the patient and/or an image of at least a part of the medical system that is reflected from the second mirror 122b to the first mirror 122a.

In the illustrated embodiments, the shielding 124, the first mirror 122a, and the second mirror 122b are configured to obviate a need to provide radiation-hard electronics for the camera 120. Thus, in some embodiments, the camera 120 comprises electronics that are not radiation-hard. For example, the electronics that are not radiation-hard may be optical sensors of the camera 120. In other embodiments, the camera 120 may include radiation-hard electronics. In such cases, the mirrors 122a, 122b and the shielding 124 may reduce a level of radiation-hard required for the electronics of the camera 120.

As shown in FIG. 5, the first mirror 122a is located inside the shielding 124, and the shielding 124 includes an opening for allowing image from the second mirror 122b to be reflected towards the first mirror 122a in the shielding 124.

In some embodiments, the first mirror 122a and/or the second mirror 122b may form part of the apparatus 100. In such cases, the apparatus 100 further includes the first mirror 122a and/or the second mirror 122b. In other embodiments, the apparatus 100 does not include the mirrors 122a, 122b.

In some embodiments, the apparatus 100 of FIG. 5 may optionally further include a processing unit (such as the processing unit 140 of FIG. 2) communicatively coupled to the camera 120. The processing unit may be configured to receive an image frame comprising the image of the first mirror 122a from the camera 120. In some embodiments, the image frame contains an image of the mirror 122a, and image of object not in the mirror 122a. In such cases, the processing unit is configured to remove a part of the image frame that does not contain the image of the first mirror 122a. In other embodiments, the entire image frame from the camera 120 captures a part of the mirror 122a. In such cases, the entire image frame from the camera 120 may be processed by the processing unit.

Figure 6A:
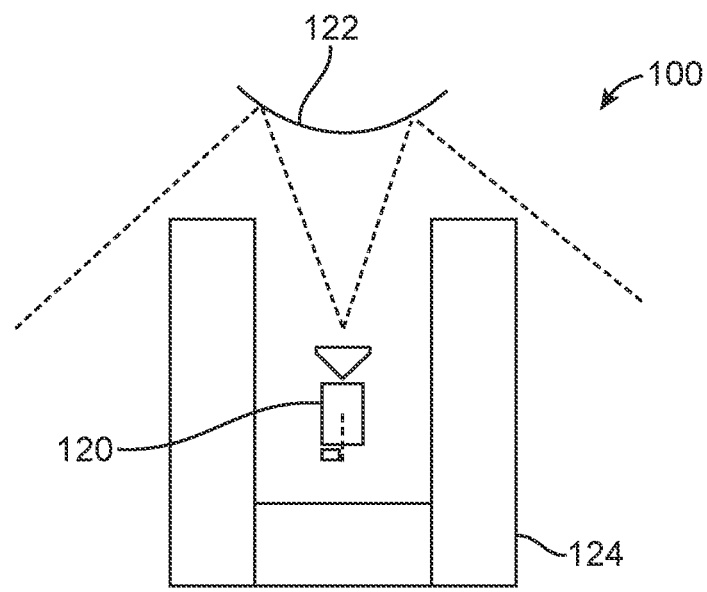
FIG. 6A illustrates another example of an apparatus that includes a camera viewing a mirror.

In some embodiments, the mirror 122 may have a curvilinear configuration. FIG. 6A illustrates another example of an apparatus 100 that includes a camera 120 viewing a mirror 122. The apparatus 100 of FIG. 6A may be an example of the apparatus 100 of FIG. 2. In the illustrated embodiments of FIG. 6A, the mirror 122 has a curvilinear configuration. By means of non-limiting examples, the mirror 122 may have a partial spherical surface, a partial aspherical shape, a partial ellipsoidal surface, a partial or a complete symmetrical cone shape, or a partial or a complete asymmetrical cone shape, or any of other curvilinear surfaces. Using a mirror with a curvilinear surface is advantageous because the camera 120 can capture a larger field of view using such mirror. In some cases, such mirror may allow the camera 120 to capture image in a 360 degree view without requiring the camera 120 to have 360-viewing capability. Also, in some embodiments, if the mirror 122 has a partial aspherical shape, such mirror may be configured to reflect image of object(s) with higher importance using a majority of its reflective surface, while a minor part of its reflective surface is configured to reflect image of object(s) with less importance.

The apparatus 100 also includes a shielding 124 that is configured to block at least some radiation resulted from an operation of a medical device. The shielding 124 surrounds at least a part of the camera 120, and includes an opening for allowing the camera 120 to view the mirror 122.

During use of the apparatus 100 of FIG. 6A, the mirror 122 reflect image of object(s) of interest (such as a patient and/or component(s) of a medical system) towards the camera 120 for imaging by the camera 120. The camera 120 generates an image frame that includes an image of the mirror 122.

Figure 6B:
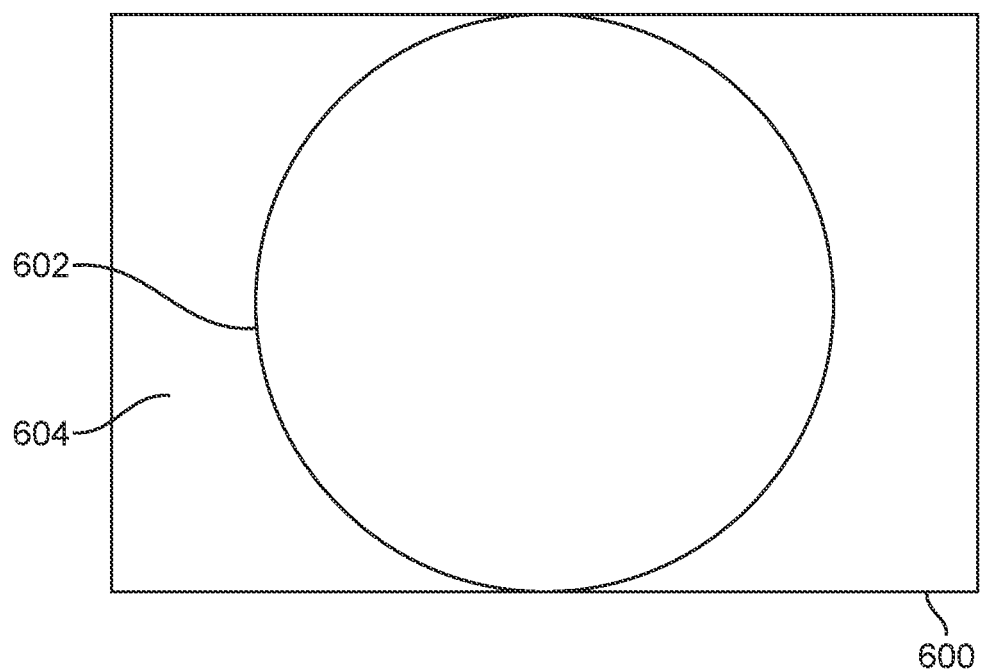
FIG. 6B illustrates an image from of the camera of FIG. 6A, particularly showing the image frame having an image of the mirror.

FIG. 6B illustrates an example of an image frame 600 output by the camera 120 of FIG. 6A, particularly showing the image frame 600 having an image 602 of the mirror 122. In the illustrated example, the mirror 122 has a circular shape, and therefore, the image frame shows the image 602 of the mirror 122 as having a circular shape. In other embodiments, the mirror 122 may have other shapes, and the image of the mirror 122 in the image frame from the camera 120 may have other shapes. Because the mirror 122 is configured to reflect image of object(s) of interest, the image 602 of the mirror 122 in the image frame 600 contains information of interest. In some embodiments, a processing unit (such as the processing unit 140 of FIG. 2) is configured to process the image frame from the camera 120, and remove (e.g., disregard) portions 604 of the image frame 600 that is outside the image 602 of the mirror 122. This reduces an amount of image data to be processed by the processing unit. After the portions 604 have been removed, the processing unit may then process the image 602 of the mirror 122.

Because the image of the mirror 122 will appear in the same location within each of the image frames that are generated by the camera 120 in a sequence, in some embodiments, the processing unit 140 may be configured to determine a location and/or a region in an image frame wherein the image of the mirror 122 will always appear. The determined location and/or region may then be stored in a non-transitory medium. During use, the processing unit 140 may retrieve the location and/or region from the non-transitory medium, and may use such information to process all image frames output by the camera 120. For example, if the stored information indicates that a circular mirror with a diameter of 4 inches will be located at X=5 inch and Y=5 inch in the image frames, the processing unit 140 may then use such information to perform filtering so that only pixels of the image of the mirror 122 will be processed and analyzed by the processing unit 140. The non-transitory medium storing the information may be located in the camera 120, or may be outside the camera 120 in communication with the processing unit 140. In other embodiments, the non-transitory medium may be integrated with the processing unit 140, or may be located in the processing unit 140.

In some embodiments, the image of object(s) (as reflected by the mirror 122) in the image 602 of the mirror 122 may be transformed by the processing unit to remove distortion resulted from surface curvature of the mirror 122 and/or from viewing angle of the camera 120 towards the mirror 122. For example, if the mirror 122 has a partial spherical surface, the image reflected off from such mirror surface will appear distorted. In such cases, the processing unit may be configured to transform the image 602 of the mirror 122 to obtain a transformed image, such that the image distortion due to the spherical mirror surface is removed. The transformed image will show image of object(s) as if the image is captured by the camera 120 viewing a flat rectilinear mirror surface. For example, in the case of a partial spherical mirror, the processor may be optionally configured to process the image of such mirror to correct for distortions caused by the curvature of the mirror surface, such as to "flatten" the image so that distortion due to curvature of the mirror surface is removed or at least reduced. In some cases, the adjusted image may be displayed to a user, and the adjusted image of the mirror may appear "flat" to a user.

Alternatively or additionally, if the camera 120 is viewing towards the mirror 122 at an angle that is non-perpendicular (or not normal) to the surface of the mirror 122, the image reflected off from such mirror surface will also appear distorted. In such cases, the processing unit may be configured to transform the image 602 of the mirror 122 to obtain a transformed image, such that the image distortion due to the non-perpendicular viewing angle between the camera 120 and the mirror 122 is removed. The transformed image will show image of object(s) as if the image is captured by the camera 120 viewing the mirror surface at a perpendicular angle.

After the image distortion (due to curvilinear mirror surface and/or non-perpendicular viewing angle between the camera 120 and the mirror 122) has been removed, the processing unit 140 may then process the image (the transformed version) of the mirror to monitor a position of the patient, to monitor a physiological state of the patient, to monitor a position of a component of the medical system, to prevent a collision between the medical device and the patient, to prevent a collision between the medical device and a patient support, or any combination of the foregoing.

In other embodiments, the processing unit 140 may not perform image distortion. In such cases, if an image from the camera 120 has distortion (e.g., due to curvature of mirror surface, and/or non-perpendicular viewing angle between the camera 120 and the mirror 122), the processing unit 140 may process the image (the non-transformed version) of the mirror to monitor a position of the patient, to monitor a physiological state of the patient, to monitor a position of a component of the medical system, to prevent a collision between the medical device and the patient, to prevent a collision between the medical device and a patient support, or any combination of the foregoing.

In the above embodiments, the image 602 of the mirror 122 has a circular portion in the image frame 600. In other embodiments, the image 602 of the mirror 122 may have other shapes in the image frame 600. For example, the image 602 of the mirror 122 may appear as having an elliptical shape, a trapezoidal shape, or any of other shapes, in the image frame 600.

Figure 7:
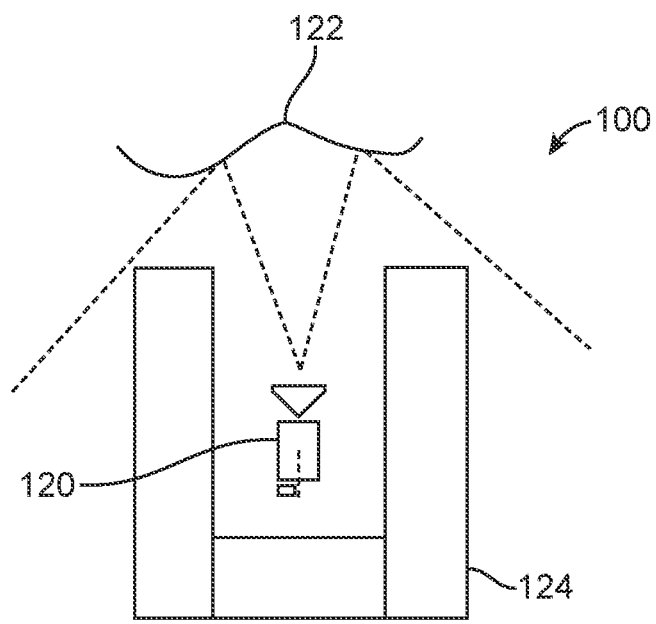
FIG. 7 illustrates another example of an apparatus that includes a camera viewing a mirror.

In other embodiments, the mirror 122 may have other shapes and surface curvatures. FIG. 7 illustrates another example of an apparatus 100 that includes a camera 120 viewing a mirror 122. As shown in the figure, the mirror 122 surface comprises both a concave surface and a convex surface.

Figure 8A:
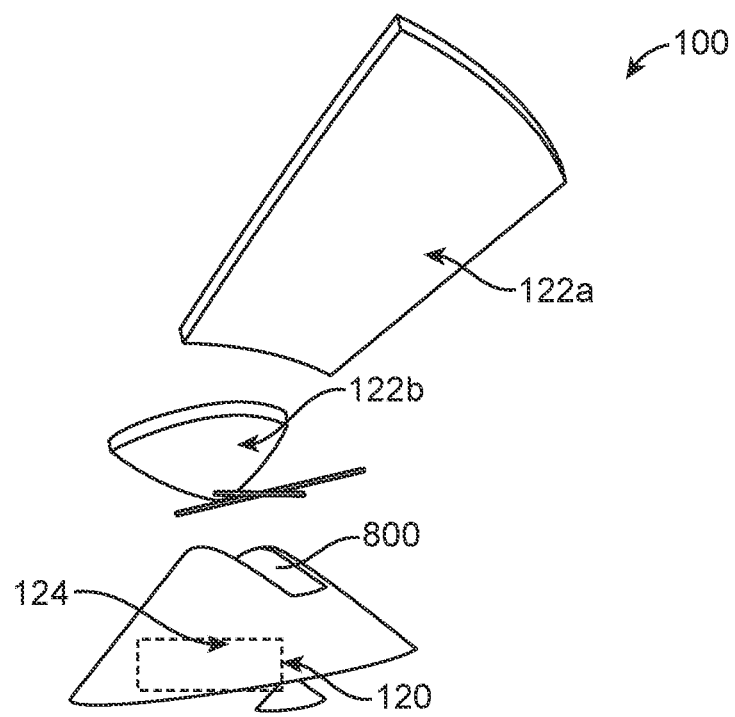
FIG. 8A illustrates another example of an apparatus that includes a camera viewing a first mirror and a second mirror, and a shielding covering at least a part of the camera.

In some embodiments, the camera 120 may be configured to view two or more mirrors simultaneously. FIG. 8A illustrates another example of an apparatus 100 that includes a camera 120 viewing a first mirror 122a and a second mirror 122b, and a shielding 124 covering at least a part of the camera 120. In the illustrated example, the first mirror 122a has a planar configuration and the second mirror 122b has a more "rounded" configuration compared to that of the first mirror 122a. In some cases, the planar configuration of the first mirror 122a is rectilinear or curvilinear. In one implementation, the first mirror 122a is a flat mirror with a slight curvature that adapts to the focal length of the camera 120. Such mirror may in some embodiments be configured to provide a frontal view. Also, in some cases, the second mirror 122b may have a partial spherical shape, a partial aspherical shape, a partial or a complete symmetrical cone shape, or a partial or a complete asymmetrical cone shape, etc. In some embodiments, the first mirror 122a and the second mirror 122b have different respective curvatures.

In some embodiments, the first mirror 122a and/or the second mirror 122b may form part of the apparatus 100. In such cases, the apparatus 100 further includes the first mirror 122a and/or the second mirror 122b. In other embodiments, the apparatus 100 does not include the mirrors 122a, 122b.

Figure 8B:
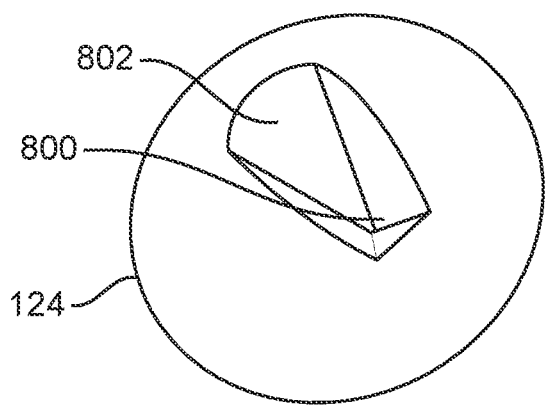
FIG. 8B illustrates the shielding of the apparatus of FIG. 8A.

FIG. 8B illustrates the shielding 124 of the apparatus 100 of FIG. 8A. As shown in FIG. 8B, the shielding 124 includes an opening 800 for allowing the camera 120 inside the shielding 124 to see the environment outside the shielding 124. The shielding 124 also includes a viewing channel 802 extending from the opening 800. The viewing channel 802 has a cross-sectional width that increases as a function of distance away from the camera 120. In other embodiments, the viewing channel 802 may have a constant cross-sectional width along at least a length of the viewing channel 802.

The first and second mirrors 122a, 122b are configured (e.g., positioned, oriented, sized, etc., or a combination of the foregoing) to reflect respective first and second areas of the environment in a medical facility. In some embodiments, the first and second areas may be mutually exclusive from each other in the sense that there is no overlap between the first and second areas. Thus, the first and second mirrors 122a, 122b are configured to reflect images of different objects for viewing by the camera 120. For example, the first mirror 122a may be configured to reflect image of at least a part of a patient for viewing by the camera 120, while the second mirror 122b may be configured to reflect image of component(s) of the medical system 10 for viewing by the camera 120, or vice versa. In other embodiments, the first and second areas may overlap. In such cases, the first and second mirrors 122a, 122b are configured to reflect images of the same object for viewing by the camera 120. The object may be at least a part of a patient or a component of the medical system 10.

Figure 8C:
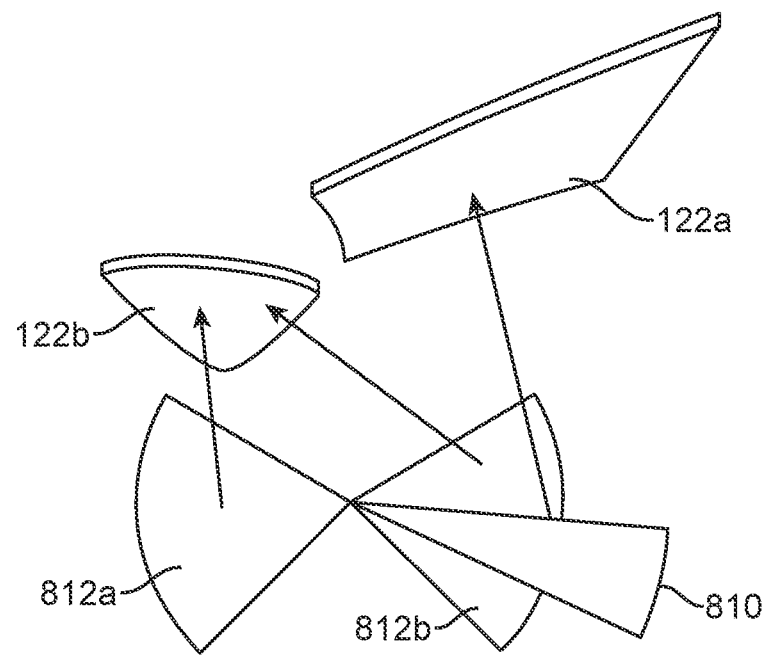
FIG. 8C illustrates the first and second mirrors of the apparatus of FIG. 8A, particularly showing the shapes of the mirrors as captured by the camera.

FIG. 8C illustrates the first and second mirrors 122a, 122b of the apparatus 100 of FIG. 8A, particularly showing areas 810, 812a, 812b in the environment that may be seen by the camera 120 via the mirrors 122a, 122b. In particular, the first mirror 122a may be configured to view the area 810 in the environment of the medical facility, and the second mirror 122*b* may be configured to view the areas 812*a*, 812*b* in the environment of the medical facility. In one example, the area 810 and the area 812*b* may cover an area where the patient is located, and the area 812*a* may cover an area where a component (e.g., a gantry, an arm, an imager, etc.) of the medical system 10 is located. In this example, both the mirrors 122*a*, 122*b* may be used by the camera to monitor the patient, while the mirror 122*b* may be used by the camera to also monitor a component of the medical system 10.

Figure 8D:
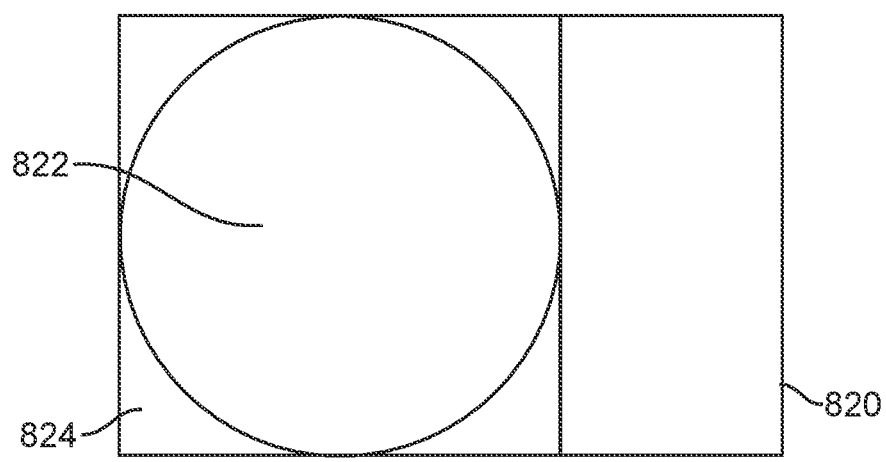
FIG. 8D illustrates an image frame of the camera of FIG. 8A, particularly showing the image frame having an image of the first mirror, and an image of the second mirror.

FIG. 8D illustrates an image frame of the camera 120 of FIG. 8A, particularly showing the image frame having an image 820 of the first mirror 122*a*, and an image 822 of the second mirror 122*b*. Because the first mirror 122*a* is configured to reflect image of object(s) of interest for viewing by the camera 120, the image 820 of the first mirror 122*a* contains image (not shown) of object(s) of interest. Similarly, because the second mirror 122*b* is configured to reflect image of object(s) of interest for viewing by the camera 120, the image 822 of the second mirror 122*b* contains image (not shown) of object(s) of interest.

During use, the camera 120 of FIG. 8A is configured to capture an image of the first mirror 122*a* and also an image of the second mirror 122*b*. In some embodiments, the camera 120 is configured to capture the image of the first mirror 122*a* and the image of the second mirror 122*b* simultaneously. In one implementation, each image frame outputted by the camera 120 includes both the image of the first mirror 122*a*, and the image of the second mirror 122*b*. The processing unit 140 is first configured to transform each of the images of the mirrors 122*a*, 122*b* in each image frame to remove distortion due to curvatures of mirror surfaces and/or due to non-perpendicular viewing angle between the camera 120 and the mirrors 122*a*, 122*b*.

After the mirror images have been transformed, the processing unit 140 may then process the images (e.g., transformed versions of the images) of the mirrors 122*a*, 122*b* to perform one or more functions. For examples, the processing unit 140 may be configured to process the image frame from the camera to monitor a position of the patient, to monitor a physiological state of the patient, to monitor a position of a component of the medical system, to prevent a collision between the medical device and the patient, to prevent a collision between the medical device and a patient support, or any combination of the foregoing.

In some embodiments, the image of the first mirror 122*a* contains a first scenery image reflected off from the first mirror 122*a*, and the image of the second mirror 122*b* contains a second scenery image reflected off from the second mirror 122*b*. The first and second scenery images may capture different objects. For example, the first scenery image may capture the patient, and the second scenery image may capture a component of the medical system 10. In such cases, the processing unit 140 may be configured to process the first scenery image and the second scenery image using different respective processing algorithms. For example, the processing unit 140 may execute a first algorithm to perform patient monitoring using the first scenery image as captured in the image of the first mirror 122*a*, and may execute a second algorithm to perform device monitoring using the second scenery image as captured in the image of the second mirror 122*b*.

In some embodiments, the processing unit 140 is also configured to split the image of the mirror 122 into subimages. For example, if the first mirror 122*a* captures images of different objects, the processing unit 140 may separately process different parts (corresponding with different respective objects) of the image of the mirror 122.

Figure 9:
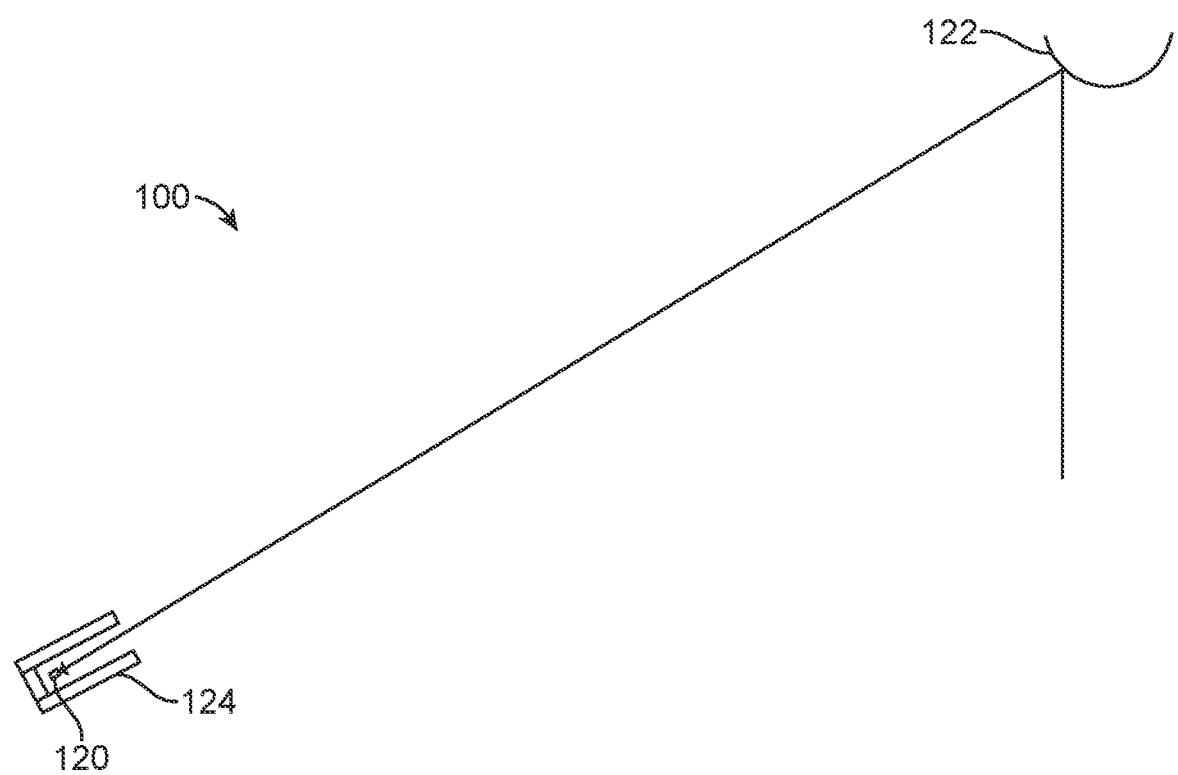
FIG. 9 illustrates another example of an apparatus that includes a camera viewing a mirror.

FIG. 9 illustrates another example of an apparatus 100 that includes a camera 120 viewing a mirror 122. The apparatus 100 of FIG. 9 may be any of the embodiments of the apparatus 100 described herein. In the illustrated embodiments, the mirror 122 is completely and physically separated from the camera 120 and its surrounding shielding 124 in that there is no mechanical linkage coupling the mirror 122 directly or indirectly to the camera 120 and/or the shielding 124. Such configuration allows the mirror 122 to be placed at a further distance from the camera 120. The distance between the camera 120 and the mirror 122 may be more than 3 feet, more than 5 feet, more than 10 feet, etc.

As mentioned, the processing unit 140 of the apparatus 100 is configured to process images from the camera 120. By means of non-limiting examples, the processing unit 140 may be configured to process images from the camera 120 to monitor a position of the patient, to monitor a physiological state of the patient, to monitor a position of a component of the medical system, to prevent a collision between the medical device and the patient, to prevent a collision between the medical device and a patient support, etc., or any combination of the foregoing. Some examples of uses and functionalities of the processing unit 140 are described below.

Patient Setup

In one method of use, the camera 120 is configured to capture, via one or more mirrors 122, image(s) of a patient, or image(s) of fiducials on or coupled to the patient. The processing unit 140 is configured to process the images from the camera 120, and determine a position (e.g., location and/or orientation) of the patient based on the processed images. Once the position of the patient is determined, the processing unit 140 may determine which direction to move the patient for patient setup, and how much to move the patient, based on a desired position of the patient to be achieved.

In some cases, a reference image may be obtained by the processing unit 140. The reference image may be generated using the camera 120 during a treatment planning session, or on the day of treatment before the treatment session. The reference image includes an image of structured light as projected onto the patient, which indicates a desired position of the patient relative to some coordinate to be achieved. During the patient setup, the camera 120 is used to generate an input image. The processing unit 140 compares the input image with the reference image to determine if they match. If not, the patient is then positioned until the input image and the reference image match.

Patient Position Monitoring

After the patient is setup, the medical system 10 may then initiate treatment of the patient by delivering treatment energy towards the patient.

During treatment, the camera 120 may continue to image the patient via one or more mirrors 122. The processing unit 140 may compare the determined position of the patient with a reference position that is determined during the patient setup. If the position of the patient deviates from the reference position by more than a threshold, then the processing unit 140 may generate a control signal to stop the delivery of the treatment energy, to move the patient to a correct position, and/or to move the treatment beam accordingly.

In some cases, the act of monitoring the position of the patient may be performed without the processing unit 140 determining the actual coordinates of the patient. In one implementation, during treatment, the camera 120 repeatedly generates input images of the patient or input images of fiducials on or coupled to the patient. The processing unit 156 processes these real-time input images by comparing each of them with the reference image. If the real-time input image matches with the reference image, then the processing unit 140 may determine that the patient has not moved, and the treatment may be allowed to continue. On the other hand, if the real-time image does not match the reference image, then the processing unit 140 may determine that the patient has moved, and the delivery of treatment energy may be stopped (e.g., in response to the processing unit 140 generating a control signal to stop the delivery of treatment). Alternatively, instead of stopping the delivery of treatment energy, the processing unit 140 may generate one or more control signals to move the patient support (couch tracking) and/or to move the beam, in order to compensate for the amount of patient movement. Movement of the beam may be accomplished by beam steering and/or by operation of the collimator.

In some embodiments, the comparing of the input image with the reference image may be performed by the processing unit 140, which performs pattern matching. In some cases, the comparison may be achieved by the processing unit 140 performing cross-correlation between the input image and the reference image. The cross-correlation results in a correlation value, which indicates a degree of match between the two-dimensional input image and the two-dimensional reference image. If the correlation value exceeds a certain pre-determined threshold (e.g., 0.9), then the processing unit 140 may determine that there is no patient movement. On the other hand if the correlation value is below a certain threshold, then the processing unit 140 may determine that the patient has moved. In other embodiments, an iterative closest point (ICP) algorithm may be used when processing the input image and the reference image.

In some embodiments, in addition or in the alternative to using input image(s) from the camera(s) 120, if TOF camera(s) is available, the processing unit 140 may use depth images from the TOF camera(s) for patient monitoring. For example, during treatment, the TOF camera(s) repeatedly generate input depth images indicating the surface profile of the patient. The processing unit 140 processes these real-time depth images by comparing each of them with a reference depth image. If the real-time depth image matches with the reference depth image, then the processing unit 140 may determine that the patient has not moved, and the treatment may be allowed to continue. On the other hand, if the real-time depth image does not match the reference depth image, then the processing unit 140 may determine that the patient has moved, and the delivery of treatment energy may be stopped (e.g., in response to the processing unit 140 generating a control signal to stop the delivery of treatment).

Respiratory Phase Determination and Treatment Control

Also, during treatment or imaging session, the camera 120 may capture, via one or more mirrors 122, images of the torso of the patient, or images of fiducial(s) on or coupled to the patient. The processing unit 140 then determines a respiratory phase and/or amplitude based on the images from the camera 120.

In one implementation, patterns of fiducials on or coupled to the patient as captured in the camera images are compared to known patterns that correspond with different breathing amplitudes or breathing phases. Accordingly, the processing unit 140 may perform patter matching based on images provided by the camera 120 to determine breathing amplitudes and/or breathing phases of the patient.

In another implementation, before a treatment session, images of the structured light as projected onto the patient may be generated and recorded as reference images. The reference images form a video showing how the structured light pattern changes during a breathing cycle of the patient. During treatment, the camera 120 provides real-time input images (as reflected by one or more mirrors 122) of the structured light as projected onto the patient while the patient is breathing. The processing unit 140 may process each real-time input image by finding one of the reference images that matches with the real-time input image. The respiratory phase for the real-time input image may then be determined as the same respiratory phase as the matched reference image. For example, if the matched reference image was generated when the patient is at breathing phase=3.6 (or during phase range from 3.0-4.0), then the real-time input image may be considered as being generated when the patient is at the same breathing phase or phase range.

In some embodiments, the determined respiratory phase or amplitude may be used to control the medical system 10. For example, the determined respiratory phase or amplitude may be used to gate a delivery of a treatment beam or imaging beam. In one implementation, if the determined respiratory phase or amplitude is within a prescribed range of phases or amplitudes for delivering treatment, then the medical system 10 is operated by the processing unit 140 (which provides a control signal) to deliver the treatment beam or the imaging beam. On the other hand, if the determined respiratory phase or amplitude is outside the prescribed range of phases or amplitudes for delivering treatment, then the medical system 10 is operated by the processing unit 140 (which provides a control signal) to stop the delivery of treatment beam or the imaging beam.

In other embodiments, the determined respiratory phase or amplitude may be used to control the medical system 10 so that the delivery of the treatment beam or the imaging beam is in synchronization with a respiratory movement of the patient. For example, the processing unit 140 may generate one or more signal to control a delivery of the treatment or imaging beam so that the treatment or imaging beam follows the movement of the patient.

Respiratory Motion Control

In some embodiments, the apparatus 100 may be configured to provide respiratory motion control. In some embodiments, the camera 120 capture, via one or more mirrors 122, image(s) of a patient or image(s) of markers coupled to the patient, and provides such images to the processing unit 140 for processing. The processing unit 140 analyzes the image(s) to determine whether a certain respiratory phase/amplitude has been achieved by the patient. For example, the processing unit 140 may determine whether a certain breath-hold amplitude has been achieved based on an analysis of the image. If a desired breath-hold amplitude has been achieved, then processing unit 140 may generate a signal to allow a medical procedure to be performed. For example, the processing unit 140 may generate a signal to allow a treatment beam to be delivered by the medical system 10. In some embodiments, the processing unit 140 may analyze a number of images from the cameras 120 overtime, to determine whether a certain breath-hold amplitude has been achieved for a certain duration (e.g., 2 seconds, 3 seconds, etc.). If a desired breath-hold amplitude has been achieved for a certain prescribed duration, then processing unit 140 may generate a signal to allow a medical procedure to be performed. For example, the processing unit 140 may generate a signal to allow a treatment beam to be delivered by the medical system 10.

In some embodiments, in addition or in the alternative to using input image(s) from the camera(s) 120, if TOF camera(s) is available, the processing unit 140 may use depth images from the TOF camera(s) to perform respiratory motion control. For example, the TOF camera(s) may generate input depth image indicating the surface profile of the patient. The processing unit 140 processes the real-time depth image to determine whether a certain respiratory control has been achieved by the patient. If a desired breath-hold amplitude has been achieved, then processing unit 140 may generate a signal to allow a medical procedure to be performed. For example, the processing unit 140 may generate a signal to allow a treatment beam to be delivered by the medical system 10. In some embodiments, the processing unit 140 may analyze a number of depth images from the TOF camera(s) overtime, to determine whether a certain breath-hold amplitude has been achieved for a certain duration (e.g., 2 seconds, 3 seconds, etc.). If a desired breath-hold amplitude has been achieved for a certain prescribed duration, then processing unit 140 may generate a signal to allow a medical procedure to be performed. For example, the processing unit 140 may generate a signal to allow a treatment beam to be delivered by the medical system 10.

Device Monitoring

It should be noted that the techniques described above should not be limited to monitoring the patient, and that they can also be employed to monitor device(s). In some embodiments, the camera 120 is configured to capture, via one or more mirrors 122, image of a part of the patient support 14, a part of the housing of the medical system 10, a part of a gantry, a part of the energy source, a part of an imaging device, a part of a positioning device, a part of an accessory, or any combination of the foregoing. In some cases, the accessory may be a positioning device, such as the Calypso device 180 (available at Varian, Palo Alto, Calif.) shown in FIG. 3. Also, in some embodiments, the accessory may be considered to be a part of the system 10.

The processing unit 140 may determine position(s) of the device(s) based on the camera images, and may compare the determined position(s) of the device(s) with respected desired position(s). If the position(s) of the device(s) deviates from the desired position(s) by more than a threshold, then the processing unit 140 may generate a control signal to stop the delivery of the treatment energy or imaging energy.

In some embodiments, in addition or in the alternative to using input image(s) from the camera(s) 120, if TOF camera(s) is available, the processing unit 140 may use depth images from the TOF camera(s) for device(s) monitoring. For example, during treatment or imaging session, the TOF camera(s) repeatedly generate input depth images indicating the surface profile(s) of the device(s). From the determined surface profile(s), the processing unit 140 may determine the position(s) of the device(s). If the position(s) of the device(s) deviates from the desired position(s) by more than a threshold, then the processing unit 140 may generate a control signal to stop the delivery of the treatment energy or imaging energy.

Patient-Machine Collision Prevention

In some embodiments, the apparatus 100 may be configured to provide patient-machine collision prevention. In some embodiments, the camera 120 may capture image of the patient, and image of one or more device surface(s), via one or more mirrors 122. The device surface(s) may be a surface of the patient support 14, a surface of the housing of the medical system 10, a surface of a gantry, a surface of the energy source, a surface of an imaging device, a surface of a positioning device, a surface of an accessory, or any combination of the foregoing. The cameras 154 provide the images to the processing unit 140 for processing. The processing unit 140 analyzes the images to determine the position of the patient and the position(s) of the device(s) being monitored. If the positon of the patient and the position of one of the device is too close (e.g., is less than a prescribed threshold), then the processing unit 140 may determine that there may be a risk of collision, and may generate a control signal to stop the operation of the medical system 10. The processing unit 140 may also generate an indicator for informing a user that there is a risk of collision. The indicator may be in a form of a visual indicator (e.g., a light, a display of an object in a screen, etc.), an audio indicator (e.g., an alarm), or both.

In some embodiments, patient monitoring may be performed simultaneously or in an interleaved manner with device monitoring. In other embodiments, patient monitoring may be performed simultaneously or in an interleaved manner with patient-machine collision prevention. In further embodiments, device monitoring may be performed simultaneously or in an interleaved manner with patient-machine collision prevention. In still further embodiments, patient monitoring, device monitoring, and patient-machine collision prevention may be performed simultaneously or in an interleaved manner. In other embodiments, any combination of the features mentioned may be performed simultaneously or in an interleaved manner.

In some embodiments, the processing unit 140 may include (1) a patient setup module configured to perform the patient setup, (2) a patient monitoring module configured to perform the patient monitoring, (3) a device monitoring module configured to perform the device monitoring, a respiratory motion controller configured to perform the respiratory motion control, and/or (4) a patient-machine collision prevention module configured to perform the patient-machine collision prevention. In some cases, the processing unit may also optionally include a device-device collision prevention module configured to perform device-to-device collision prevention. For example, the processing unit may be configured to monitor the moving gantry and the patient support to prevent collision between these two devices. As another example, the processing unit may be configured to monitor an imaging panel (e.g., a kV panel) and a position detection device (e.g., a Calypso console) to prevent collision between these two devices.

Also, in some embodiments, the input image(s) from the camera(s) 120 may be real-time image(s). For example, the camera(s) 120 may be configured to repeatedly generate real-time input images, and the processing unit 140 processes these input images in real-time (e.g., within a short time after the image is generated, such as within 1 second, and more preferably within 0.5 second, and more preferably within 0.1 second) to monitor the position(s) of the component(s) of the system 10, and/or position of the patient.

It should be noted that the apparatus 100 described herein is not limited to application with medical systems that provide radiation treatment beams, and that the apparatus 100 may be employed in other types of medical system and procedures. For example, in other embodiments, the medical system 10 may be configured to provide proton beam, and the apparatus 100 described herein may be used during a proton treatment procedure. As another example, the medical system 10 may be configured to provide imaging beam, and the apparatus 100 described herein may be used during an imaging session. In some cases, the imaging may be performed using a CT machine, which may be a stationary machine, or a machine that is moveably coupled to a rail. Also, as used in this specification, the term "radiation" may include "proton beam", a beam for treatment, or a beam for imaging.

It should be noted that the uses and functionalities of the processing unit 140 are not limited to be above examples, and that the processing unit 140 may be configured to perform other functions in other embodiments.

Figure 10:
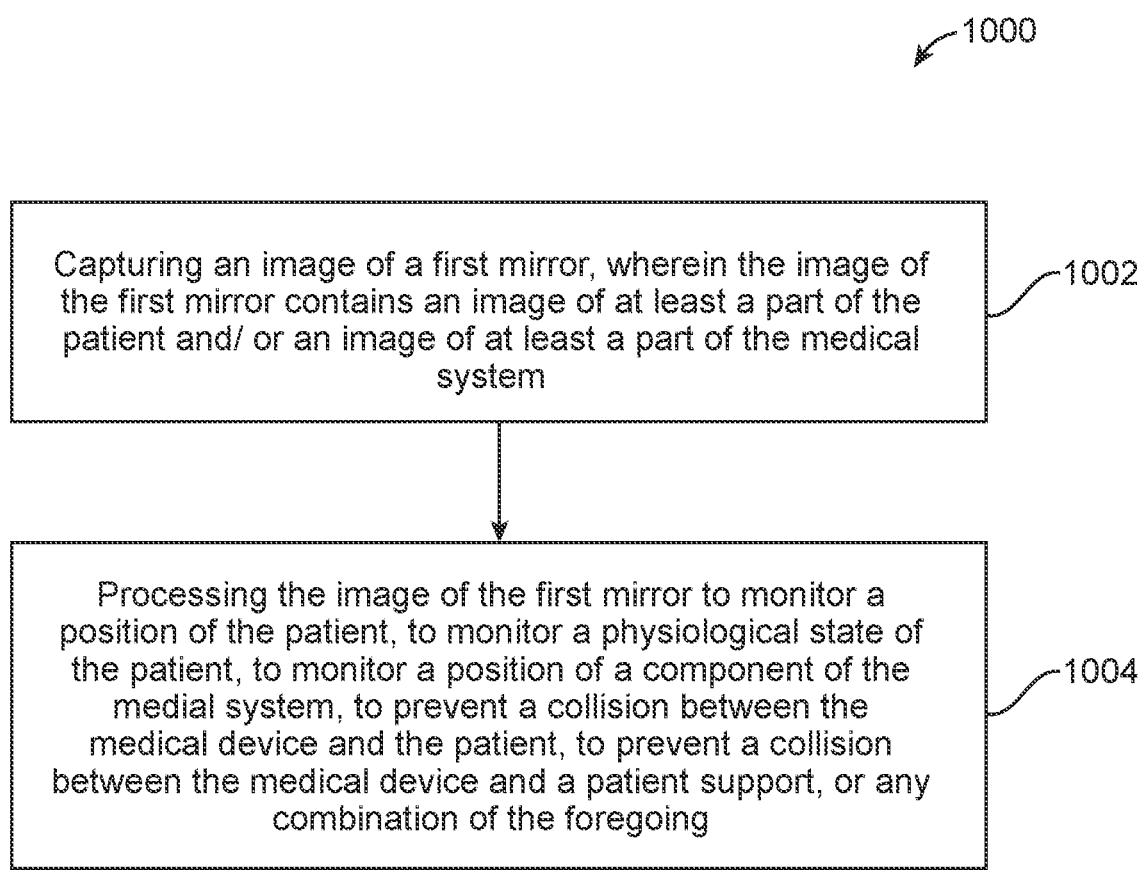
FIG. 10 illustrates a method in accordance with some embodiments.

FIG. 10 illustrates a method 1000 that may be performed by an apparatus that is configured for use with a medical system. The medical system may comprise a medical device configured to treat a patient. The apparatus performing the method 1000 may be the apparatus 100 of FIG. 1-6A, 7, 8A, or 9. The method 1000 includes capturing an image of a first mirror, wherein the image of the first mirror contains an image of at least a part of the patient and/or an image of at least a part of the medical system (item 1002). The method 1000 also includes processing the image of the first mirror to monitor a position of the patient, to monitor a physiological state of the patient, to monitor a position of a component of the medical system, to prevent a collision between the medical device and the patient, to prevent a collision between the medical device and a patient support, or any combination of the foregoing (item 1004).

Specialized Processing System

Figure 11:
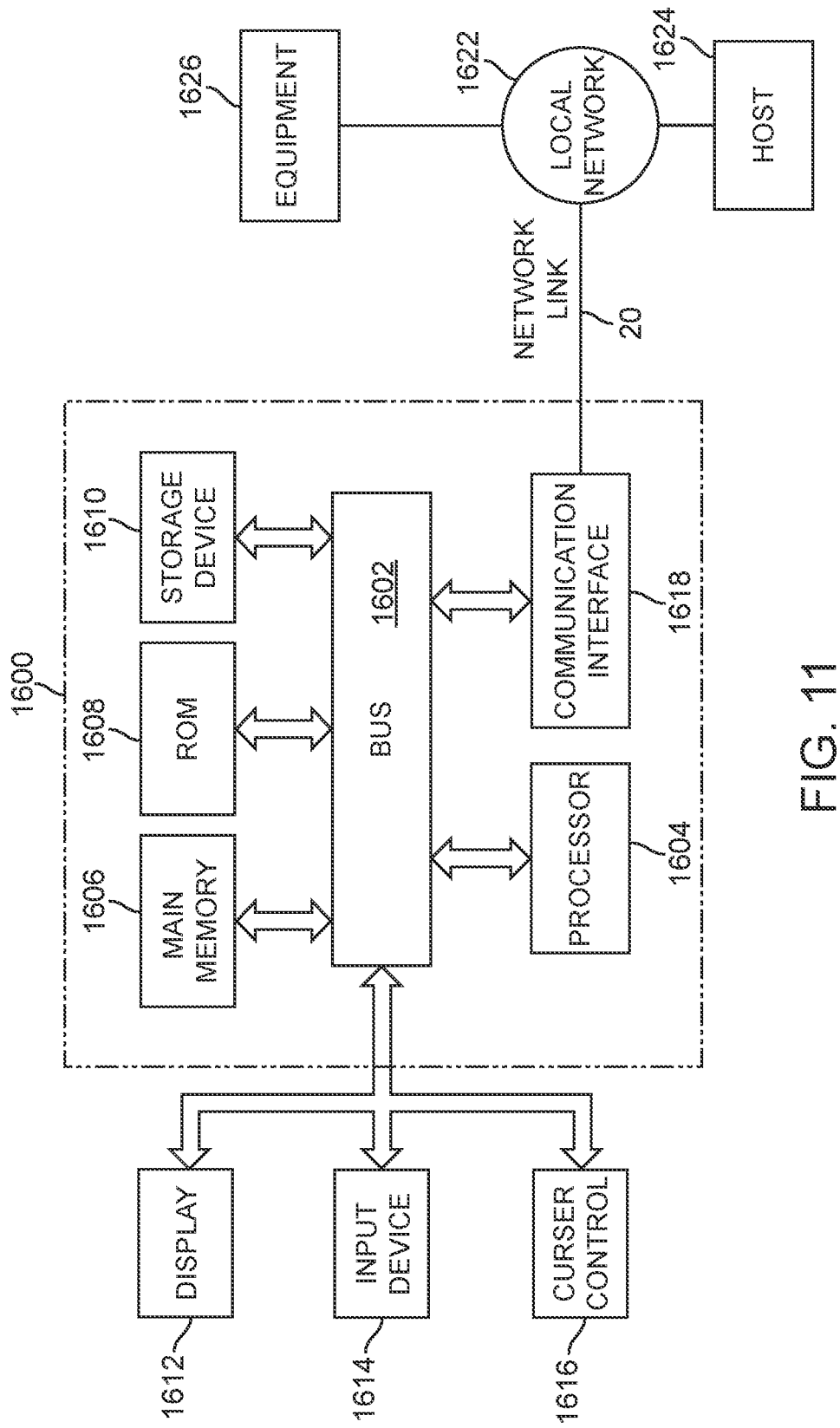
FIG. 11 is a diagram of a processing system with which embodiments described herein may be implemented.

FIG. 11 is a block diagram illustrating an embodiment of a specialized processing system 1600 that can be used to implement various embodiments described herein. For example, the processing system 1600 may be configured to process images from camera(s) 120 in accordance with some embodiments. Also, in some embodiments, the processing system 1600 may be used to implement the processing unit 140 of FIG. 2, the processing unit 156 of FIG. 3 or FIG. 4, and/or the processing unit 54 of FIG. 1, 3 or 4. In some embodiments, the processing unit 140/156 of the apparatus 100 may integrate with, or may be implemented using, the control 40 and/or the processing unit 54 described herein. The processing system 1600 may also be an example of any processing unit described herein.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a flat panel, for displaying information to a user. An input device 1614, including alphanumeric and other keys, or a touchscreen, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a network, such as the Internet or a local network. A receiving unit local to the processing system 1600 can receive the data from the network, and provide the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

The following items are exemplary features of embodiments described herein. Each item may be an embodiment itself or may be a part of an embodiment. One or more items described below may be combined with other item(s) in an embodiment.

Item 1: An apparatus for use with a medical system, the medical system comprising a medical device configured to treat and/or image a patient, includes: a camera configured to capture an image of a first mirror; wherein the image of the first mirror contains an image of at least a part of the patient and/or an image of at least a part of the medical system.

Item 2: The camera comprises electronics that are not radiation-hard or that are partially radiation-hard.

Item 3: The apparatus further includes a shielding covering a part of the camera, wherein the shielding is configured to block at least some radiation resulted from an operation of the medical device.

Item 4: The shielding and the first mirror are configured to obviate a need to provide radiation-hard electronics for the camera.

Item 5: The shielding comprises an opening aligned with a viewing path of the camera, wherein the opening is configured to allow the camera to view the first mirror.

Item 6: The apparatus further includes a processing unit configured to receive an image frame comprising the image of the first mirror from the camera.

Item 7: The processing unit is also configured to remove a part of the image frame that does not contain the image of the first mirror.

Item 8: The processing unit is also configured to split the image of the first mirror into sub-images.

Item 9: The processing unit is configured to process the image frame from the camera to monitor a position of the patient, to monitor a physiological state of the patient, to monitor a position of a component of the medical system, to prevent a collision between the medical device and the patient, to prevent a collision between the medical device and a patient support, or any combination of the foregoing.

Item 10: The apparatus further includes the first mirror.

Item 11: The first mirror comprises a flat mirror.

Item 12: The first mirror comprises a curvilinear mirror.

Item 13: The first mirror comprises an asymmetric mirror.

Item 14: The first mirror is detachably coupled to a part of the apparatus.

Item 15: The camera is also configured to capture an image of a second mirror.

Item 16: The camera is configured to capture the image of the first mirror and the image of the second mirror simultaneously.

Item 17: The apparatus further includes the first mirror and the second mirror, wherein the first mirror and the second mirror have different respective curvatures.

Item 18: The apparatus further includes the first mirror and the second mirror; wherein the first mirror has a planar configuration that is either rectilinear or curvilinear, and the second mirror has a partial spherical shape, a partial aspherical shape, a partial or a complete symmetrical cone shape, or a partial or a complete asymmetrical cone shape.

Item 19: The apparatus further includes a processing unit configured to process an image frame from the camera, wherein the image frame comprises the image of the first mirror and the image of the second mirror.

Item 20: The image of the first mirror contains a first scenery image reflected off from the first mirror, and the image of the second mirror contains a second scenery image reflected off from the second mirror; and wherein the processing unit is configured to process the first scenery image and the second scenery image using different respective processing algorithms.

Item 21: The apparatus is configured to be mounted to a patient support.

Item 22: The camera is configured to be mounted to the medical device, and herein the medical device is a treatment machine or an imaging machine.

Item 23: The camera is configured to be mounted directly or indirectly to a wall, a ceiling, a beam, or a column.

Item 24: The electronics that are not radiation-hard comprise optical sensors of the camera.

Item 25: An apparatus for use with a medical system, the medical system comprising a medical device configured to treat and/or image a patient, includes: a camera configured to capture an image of a first mirror, wherein the image of the first mirror contains an image of at least a part of the patient and/or an image of at least a part of the medical system; and a processing unit configured to receive an image frame from the camera, the image frame comprising the image of the first mirror; wherein the processing unit is also configured to extract the image of the first mirror from the image frame, and process the image of the first mirror to monitor a position of the patient, to monitor a physiological state of the patient, to monitor a position of a component of the medical system, to prevent a collision between the medical device and the patient, to prevent a collision between the medical device and a patient support, or any combination of the foregoing.

Item 26: A method performed by an apparatus that is configured for use with a medical system, the medical system comprising a medical device configured to treat and/or image a patient, includes: capturing an image of a first mirror, wherein the image of the first mirror contains an image of at least a part of the patient and/or an image of at least a part of the medical system; and processing the image of the first mirror to monitor a position of the patient, to monitor a physiological state of the patient, to monitor a position of a component of the medical system, to prevent a collision between the medical device and the patient, to prevent a collision between the medical device and a patient support, or any combination of the foregoing.

Also, it should be noted that as used in this specification, the term "image" is not limited to an image that is displayed, and may refer to an image that is not displayed (e.g., an image in data or digital form that is stored).

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

What is claimed:

1. An apparatus for use with a medical system, the medical system comprising a medical device configured to at least one of treat a patient or image the patient, the apparatus comprising:
   a camera configured to capture an image of a first mirror; and
   a processor configured to receive an image frame comprising the image of the first mirror from the camera and remove a part of the image frame that does not contain the image of the first mirror,
   wherein the image of the first mirror contains at least one of an image of at least a part of the patient or an image of at least a part of the medical system.

2. The apparatus of claim 1, wherein the camera comprises electronics that are not radiation-hard or that are partially radiation-hard.

3. The apparatus of claim 1, further comprising a shielding covering a part of the camera, wherein the shielding is configured to block at least some radiation resulted from an operation of the medical device.

4. The apparatus of claim 3, wherein the first mirror is removably coupled to the camera such that a relative orientation between the first mirror and the camera is selectively adjustable.

5. The apparatus of claim 3, wherein the shielding comprises an opening aligned with a viewing path of the camera, wherein the opening is configured to allow the camera to view the first mirror.

6. The apparatus of claim 1, wherein the processor is also configured to split the image of the first mirror into sub-images.

7. The apparatus of claim 1, wherein the processor is configured to process the image frame from the camera to monitor a position of the patient, to monitor a physiological state of the patient, to monitor a position of a component of the medical system, to prevent a collision between the medical device and the patient, to prevent a collision between the medical device and a patient support, or any combination of the foregoing.

8. The apparatus of claim 1, wherein the first mirror comprises an asymmetric mirror.

9. The apparatus of claim 1, wherein the camera is also configured to capture an image of a second mirror.

10. The apparatus of claim 9, wherein the first mirror and the second mirror have different respective curvatures.

11. The apparatus of claim 9, wherein the first mirror has a planar configuration that is rectilinear or curvilinear, and the second mirror has a partial spherical shape, a partial aspherical shape, a partial or a complete symmetrical cone shape, or a partial or a complete asymmetrical cone shape.

12. The apparatus of claim 9, wherein the image frame comprises the image of the first mirror and the image of the second mirror.

13. The apparatus of claim 12, wherein:
   the image of the first mirror contains a first scenery image reflected off from the first mirror;
   the image of the second mirror contains a second scenery image reflected off from the second mirror; and
   the processor is configured to process the first scenery image and the second scenery image using different respective processing algorithms.

14. The apparatus of claim 1, wherein the medical device is a treatment machine or an imaging machine, and wherein the camera is configured to be mounted to a patient support in the medical system, to the treatment machine, or to the imaging machine.

15. The apparatus of claim 1, wherein the camera is configured to be mounted directly or indirectly to a wall, a ceiling, a beam, or a column.

16. An apparatus for use with a medical system, the medical system comprising a medical device configured to at least one of treat a patient or image the patient, the apparatus comprising:
   a camera configured to capture an image of a first mirror, wherein the image of the first mirror contains at least one of an image of at least a part of the patient or an image of at least a part of the medical system; and
   a processor configured to receive an image frame from the camera, the image frame comprising the image of the first mirror,
   wherein the processor is also configured to remove a part of the image frame that does not contain the image of the first mirror, extract the image of the first mirror from the image frame, and process the image of the first mirror to monitor a position of the patient, to monitor a physiological state of the patient, to monitor a position of a component of the medical system, to prevent a collision between the medical device and the patient, to prevent a collision between the medical device and a patient support, or any combination of the foregoing.

17. A method performed by an apparatus that is configured for use with a medical system, the medical system comprising a medical device configured to at least one of treat a patient or image the patient, the method comprising:
   capturing an image of a first mirror, wherein the image of the first mirror contains at least one of an image of at least a part of the patient or an image of at least a part of the medical system;
   receiving an image frame comprising the image of the first mirror;
   removing a part of the image frame that does not contain the image of the first mirror; and
   processing the image of the first mirror to monitor a position of the patient, to monitor a physiological state of the patient, to monitor a position of a component of the medical system, to prevent a collision between the medical device and the patient, to prevent a collision between the medical device and a patient support, or any combination of the foregoing.

* * * * *